United States Patent

Koros et al.

[11] Patent Number: 5,980,522
[45] Date of Patent: Nov. 9, 1999

[54] EXPANDABLE SPINAL IMPLANTS

[76] Inventors: Tibor Koros; Gabriel Koros, both of 610 Flinn Ave., Moorpark, Calif. 93021

[21] Appl. No.: 08/976,205

[22] Filed: Nov. 21, 1997

Related U.S. Application Data

[63] Continuation-in-part of application No. 29/027,857, Jul. 22, 1994, Pat. No. Des. 397,439.

[51] Int. Cl.$^6$ .................................................. A61B 17/56
[52] U.S. Cl. .............................. 606/61; 606/60; 606/62; 606/63; 623/17
[58] Field of Search ................................ 606/61, 62, 60, 606/73, 86, 87; 623/17

[56] References Cited

U.S. PATENT DOCUMENTS

| | | | |
|---|---|---|---|
| 4,961,740 | 10/1990 | Ry et al. | 606/61 |
| 5,015,247 | 5/1991 | Michelson | 606/61 |
| 5,055,104 | 10/1991 | Ray | 606/61 |
| 5,192,327 | 3/1993 | Brantigan | 623/17 |

*Primary Examiner*—Michael Buiz
*Assistant Examiner*—(Jackie) Tan-Uyen Thi Ho
*Attorney, Agent, or Firm*—Richard Slehofer

[57] ABSTRACT

The invention is an expandable box-shaped spinal implant used to fuse adjacent vertebra in the patient's spine. The implant includes three interlocking parts, which are the superior section, the inferior section, and the U-shaped expander cap. The Box-shaped expandable spinal implant is formed by mating the superior section and the inferior section. The superior section has a top, a pair of mirror image vertical sides, and an upper proximal face. The inferior section has a bottom, a pair of mirror image vertical sides, and a lower proximal face. The pair of mirror image vertical sides on the superior section and the pair of mirror image vertical sides on the inferior section overlap each other and have guide way means and locking means to allow the upper section and the lower section to slideably expand transversely relative to each other. The superior and inferior sections form a closed end and an open end. A pair of exterior longitudinal channels are formed where the pair of vertical sides overlap. The U-shaped expander cap is formed by a pair of opposed prongs and a sealing cap for coupling with the superior and inferior sections. The pair of opposed prongs on the expander is positionable in the pair of expandable channels on the sides of the superior and inferior sections to force the sections slightly apart as the cap abuts the open end of the sections. The U-shaped expander locks the sections together while the cap on the expander seals off the open end of the implant.

3 Claims, 7 Drawing Sheets

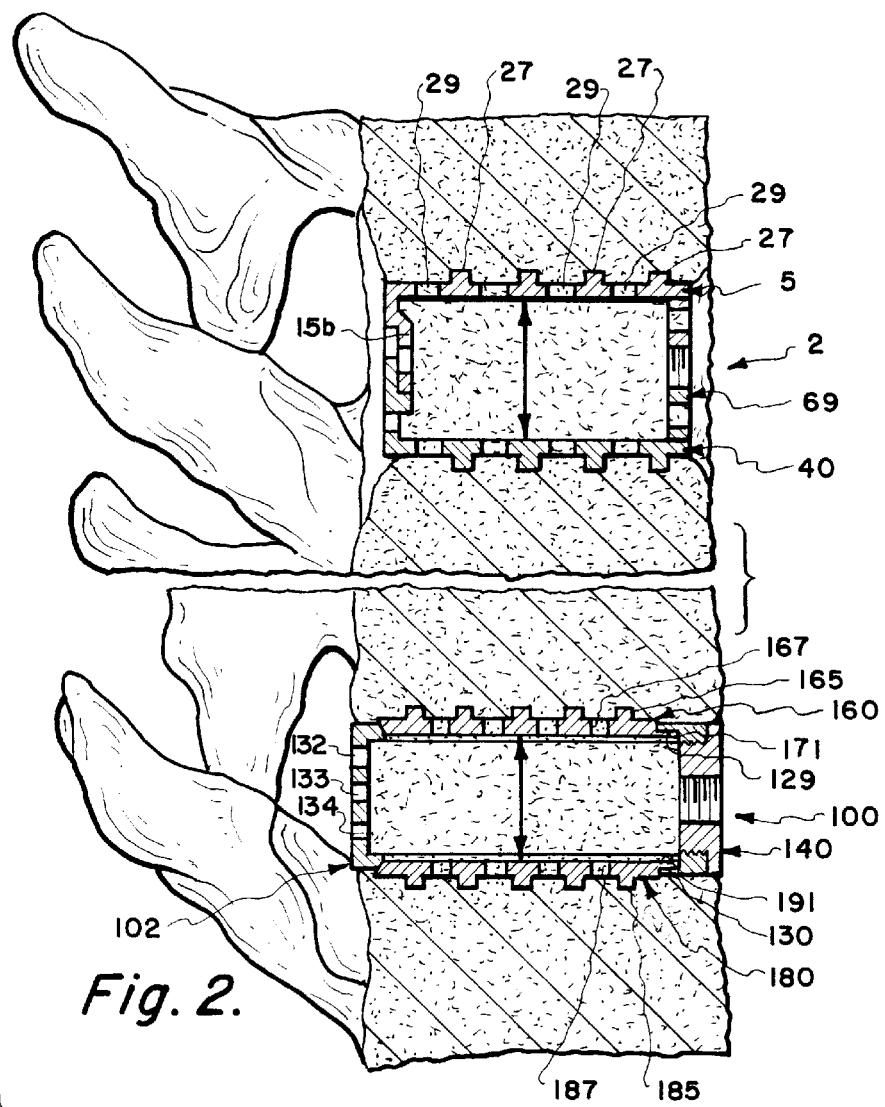
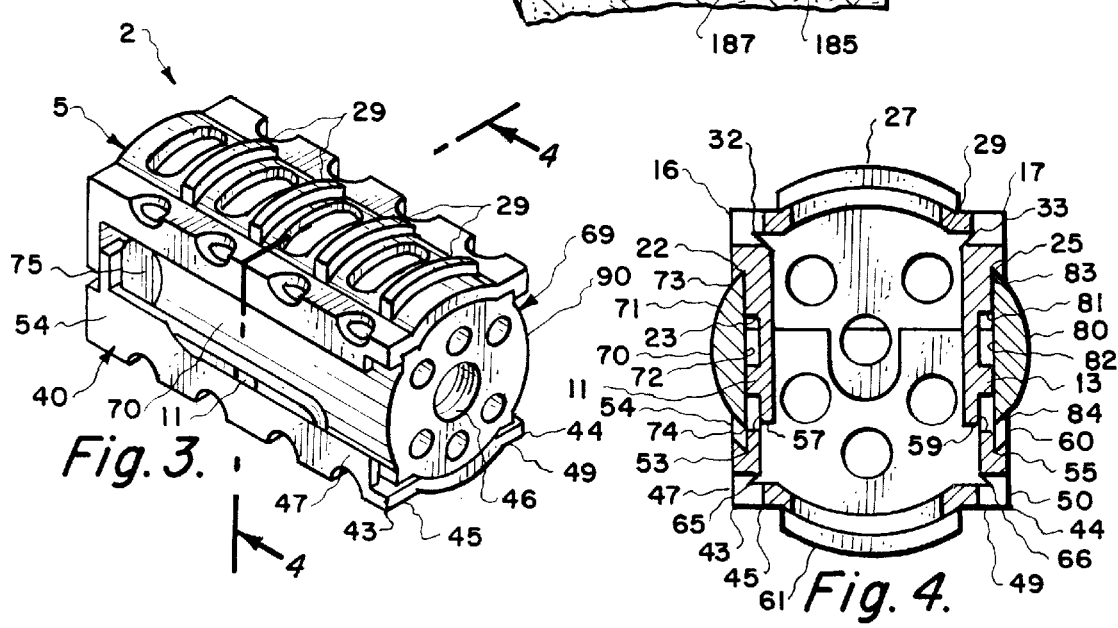

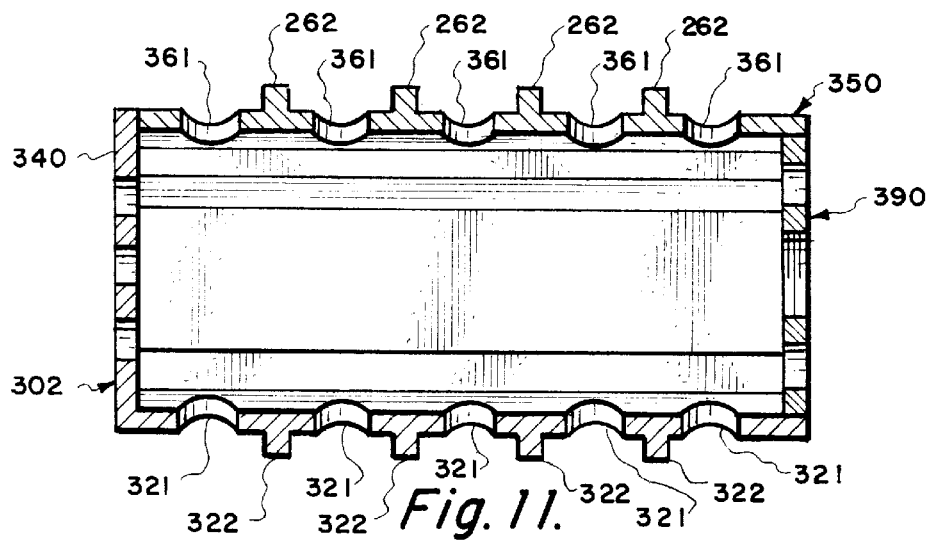
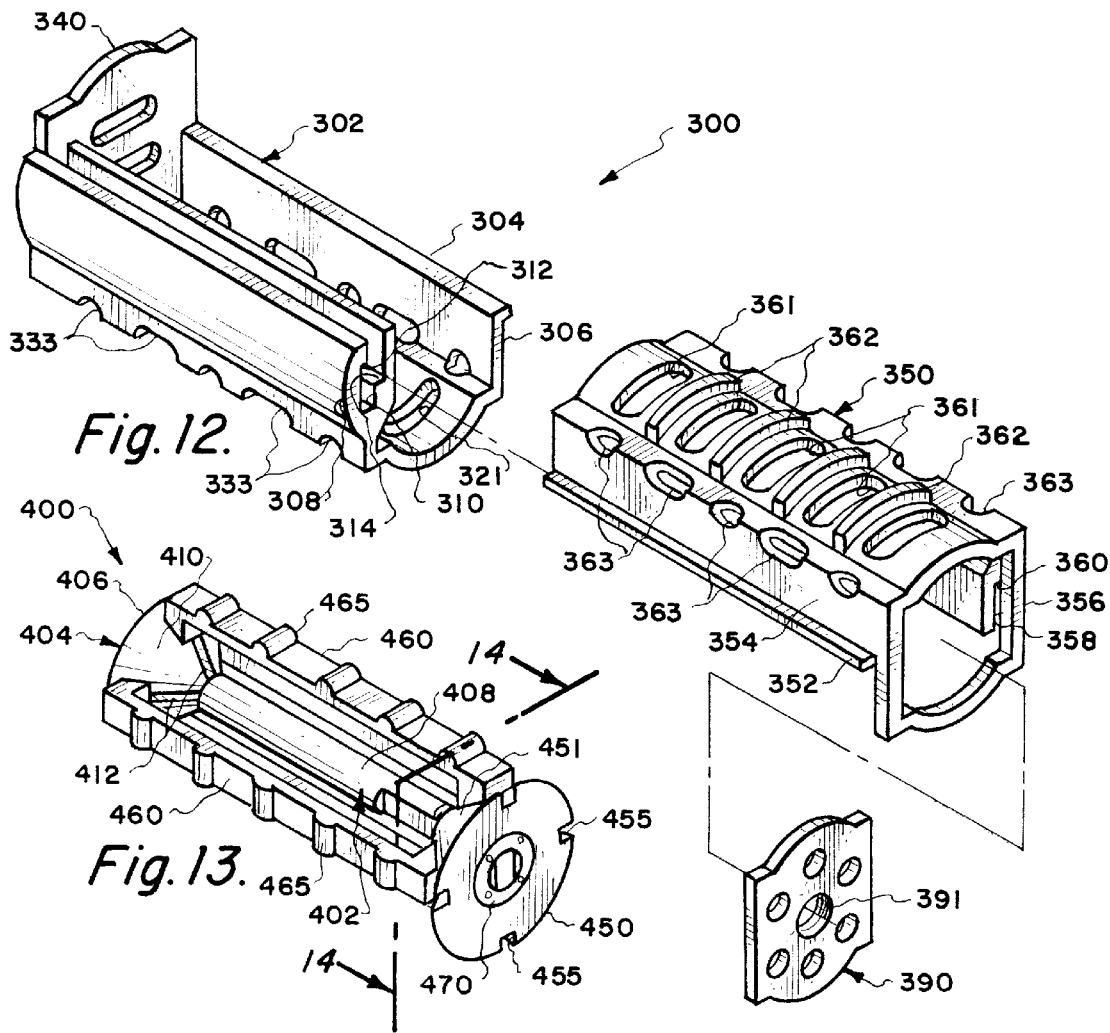

EXPANDABLE SPINAL IMPLANTS

CROSS REFERENCE TO RELATED APPLICATIONS

This is a continuation-in-part of patent application Ser. No. 29/027,857, which was filed on Jul. 22, 1994, now U.S. Pat. No. Des. 397,439.

BACKGROUND OF THE INVENTION

1. Field of the Invention

The present invention pertains to the following areas of technology:

PROSTHESIS (I.E., ARTIFICIAL BODY MEMBERS), PARTS THEREOF OR AIDS AND ACCESSORIES THEREFOR; implantable prosthesis for the spinal column such as vertebrae and spinal discs for example.

2. Description of the Prior Art:

U.S. Pat. No. 4,501,269 issued to Bagby on Feb. 26, 1985 discloses a basket-type of spinal implant.

U.S. Pat. No. 4,961,740 issued on Oct. 9, 1990 to Ray and U.S. Pat. No. issued on Oct. 8, 1991 also issued to Ray disclose a coil-type of spinal implant.

U.S. Pat. No. 5,015,247 issued on May 14, 1991 to Michelson discloses a threaded spinal implant.

In the early 1950's an operation was pioneered by Ralph B. Cloward, M.D. for the removal of ruptured cervical disc lesions and osteophytes by an anterior surgical approach. A herniated disc is a rupture or herniation of the intervertebral disc, especially between lumbar vertebrae. This usually causes pain in the affected side. An osteophyte is a bony excrescence or out-growth, which is usually branched in shape. The anterior surgical approach means that a transverse incision is made on the patient's throat just to the right of the wind pipe. The level of the lesions is identified before the operation either by injecting methylene blue dye into the disc under X-ray control the day before surgery or by a portable X-ray taken in the operating room with the needle inserted into the disc. Endotracheal general anaesthesia is used in most cases. The patient is placed in the supine position with the neck extended over a special neck rest. It is soft but firm and X-ray's can be taken through it. The head is turned to the left and secured to the table with an adhesive band across the forehead.

The location of the transverse incision is determined by the level of the lesion. The C5-6 disc lies beneath the cricoid cartilage and the adjacent disc one centimeter above or below. The various neck muscles and nerves are cut so that the anterior of the spinal cord is eventually exposed. A small rectangular retractor is placed around the disc area so that the surgeon has room within which to work. The disc that has the lesions is removed with a rongeur and a scalpel. The main objective of the Cloward procedure is to make at least one drill hole between the adjoining vertebrae to a sufficient depth but yet to prevent it from damaging any of the nerves contained within the spinal cord. After the drill hole has been completed, a complementary bone plug is removed from the patient's hip. The bone plug from the patient's hip is then positioned into the drill hole made in the pair of vertebrae. The hip bone plug will then fuse with the two vertebrae to create one vertebra that is fused together.

The guide used for the drill hole is usually placed slightly off center to the right of the midline regardless of lateralization of lesion so the drill will remove more bone on the right side. The bottom of the drill guard has pins which have to be hammered into the surface of the vertebrae to secure the drill guard for the operation. The guard pins on the drill guard do not harm the spinal cord because of the neck rest under the neck. Three drill tip sizes are available in diameters of 11.5 mm, 13.5 mm, and 15.5 mm, to accommodate the variation and the size of the vertebral bodies and the width of the disc spaces. The drill tips are interchangeable on a single drill shaft and are adjustable in length with the guard. A relief opening in the drill guard permits escape of bone dust and prevents the drill from binding. When drilling is complete, the guard and drill are removed and the drill hole immediately fill with a gel foam pad soaked in topical thrombin and packed with a padding.

The dowel is attached to the impactor tip. If the bone graft is too long or too large it can be tailored with a file to the appropriate size. Some surgeons are apprehensive that the dowel may be driven into the spinal canal damaging the spinal cord. This is a serious but avoidable complication. It can be prevented by using a dowel impactor tip larger then the drill hole. This will permit the dowel to be inserted only flush with the vertebra. It must then be recessed slightly with the smaller impactor two millimeters below the outer rim of the drill hole. Heavy pounding is unnecessary and should not be done. The distance between the dura and the inner end of the dowel can be determined by lowering the osteophyte elevator into the interspace lateral to the drill hole. The foot of the elevator is placed beneath the dowel and raised gently up and down.

With the wound closure, the two retractor blades are removed and the longus colli muscle is checked for bleeding points. Any bleeding from the outer margin of the drill hole or the guard pin holes can be arrested with bone wax.

Post operative pain from this operation is minimal and is controlled with mild analgesics. The patient is permitted to be up the day of the operation. Movements of neck are not restricted and no neck brace cast is required. A soft cervical collar is used for multiple level cases.

The patient is usually discharged from the hospital on the third or fourth day. X-rays are taken prior to discharge to determine the position of the bone graft or grafts and for comparison with subsequent follow-up films.

The parts which comprise the Cloward kit include: the skin retractor; cervical muscle retractor; blade retractor; cervical periosteal elevator; cervical retractor (large) with set of seven sharp blades; double hinged retractor handle; cervical retractor with seven blunt blades; rongeur; cervical vertebra spreader; depth gauge; the three drill tips of the three sizes previously mentioned; drill shaft with depth stop and drill guard; guard guide; drill guard cap; cervical hammer; cross bar handle; bone punch; tissue retractor; dowel cutter shaft; dowel cutter center pin; dowel holder; dowel handle and impactor set; and a curved cervical osteotome 4 mm in size.

SUMMARY AND OPERATION OF THE INVENTION

The present invention is an expandable spinal implant used to fuse adjacent vertebra in the patient's spine. Four embodiments of the expandable implant invention are disclosed. They are the box implant, the cylinder implant, the shell implant, and the reel implant.

The box implant includes three interlocking parts. The three interlocking parts are the superior section, the inferior section, and the U-shaped expander cap. The surgical hole previously prepared by the surgeon somewhat box-shaped. The four corners have V-shaped cuts to receive the four edges of the box implant and to prevent turning of the implant long after the operation has taken place. After the surgeon has made the intervertebral hole in the patient's spine as illustrated in FIG. 1, the box implant is packed full with bone chips and perhaps other organic matter. The expander cap is then partially slipped onto the other two sections as illustrated in FIG. 1. The two sections are at their resting minimum height. The box implant is inserted fully into the surgical hole until the proximal end is below the surface of the adjacent vertebrae. The expander cap is then pushed and locked into place on the implant until the cap forms a flush front surface. As the tips of the expander cap reach the risers but before the stop limits on the superior and inferior sections of the box implant, the two sections expand as shown in FIG. 2 so that the superior and inferior transverse ribs penetrate the superior and inferior surfaces of the surgical hole to lock the implant in place.

The second embodiment can be described as a cylinder-shaped expandable spinal implant. The second embodiment includes four components. They are a hollow housing, a cap, an upper separate removable arcuate section, and a lower separate removable arcuate section. The cap has a threaded center bore. This bore is used to receive the threaded tip of an instrument, which in turn is used to thread the cap into the housing after the housing and arcuate sections have been positioned into the surgical hole previously drilled in the patient's adjacent vertebrae. Four transverse slotted openings are located between transverse ribs on the movable arcuate sections. The slots allow for bone and tissue penetration and growth after the cylinder implant has been surgically implanted in a patient, as shown in FIGS. 1–2. The interior of the cylinder implant is packed with bone chips just before the cap is screwed onto the end of the implant. The cap compresses the bone chips, which in turn force the arcuate sections outwardly against the wall of the surgical drill hole to prevent the implant from loosening long after the surgery. The proximal end of an example of a typical instrument is shown in broken lines in FIG. 1. The cap also has a pair of small holes. These holes and the center bore allow bone and soft tissue to grow into the implant after the operation. The end result is the implant and the adjacent vertebrae fuse together. The surgical drill hole for receiving the cylinder implant and the tip of the instrument used for placing the implant in the hole are illustrated in FIG. 1.

The third embodiment can be described as a two-piece shell expandable spinal implant. The third embodiment shell implant has three separate components. They are the lower shell, the upper shell, and the locking distal plate.

The fourth embodiment can be described as a reel-shaped expandable spinal implant. The implant has six separate components. They are a bolt, a nut and four support braces. The nut is screwed onto the threaded end of the central rod. By tightening the nut, the cap is caused to slide towards the bolt head. Keys on the ends of the braces slide outwardly and radially to expand the four braces until the implant is securely locked into position in the surgical hole in the vertebrae previously drilled and prepared by the surgeon for receiving the implant. Prior to tightening the nut, the open space between the central rod and the four braces is packed with bone chips so that the implant will fuse with the adjacent vertebrae after implantation.

BRIEF DESCRIPTION OF THE DRAWINGS

FIG. 2 is a vertical sectional view of FIG. 1 of the first and the second embodiments of the present spinal implant invention after the spinal implants have been surgically implanted in a patient's vertebrae.

FIG. 3 is a perspective view of the first embodiment of the present spinal implant invention as shown in FIG. 1, with the implant closed.

FIG. 4 is a transverse sectional view taken along the line 4—4 of FIG. 3.

FIG. 11 is a longitudinal sectional view taken along the line 11—11 of FIG. 10.

FIG. 12 is an exploded sectional view of the third embodiment of the present invention.

FIG. 13 is a perspective view of the fourth or reel embodiment of the present invention.

DETAILED DESCRIPTION OF THE FOUR EMBODIMENTS

Figure 1:
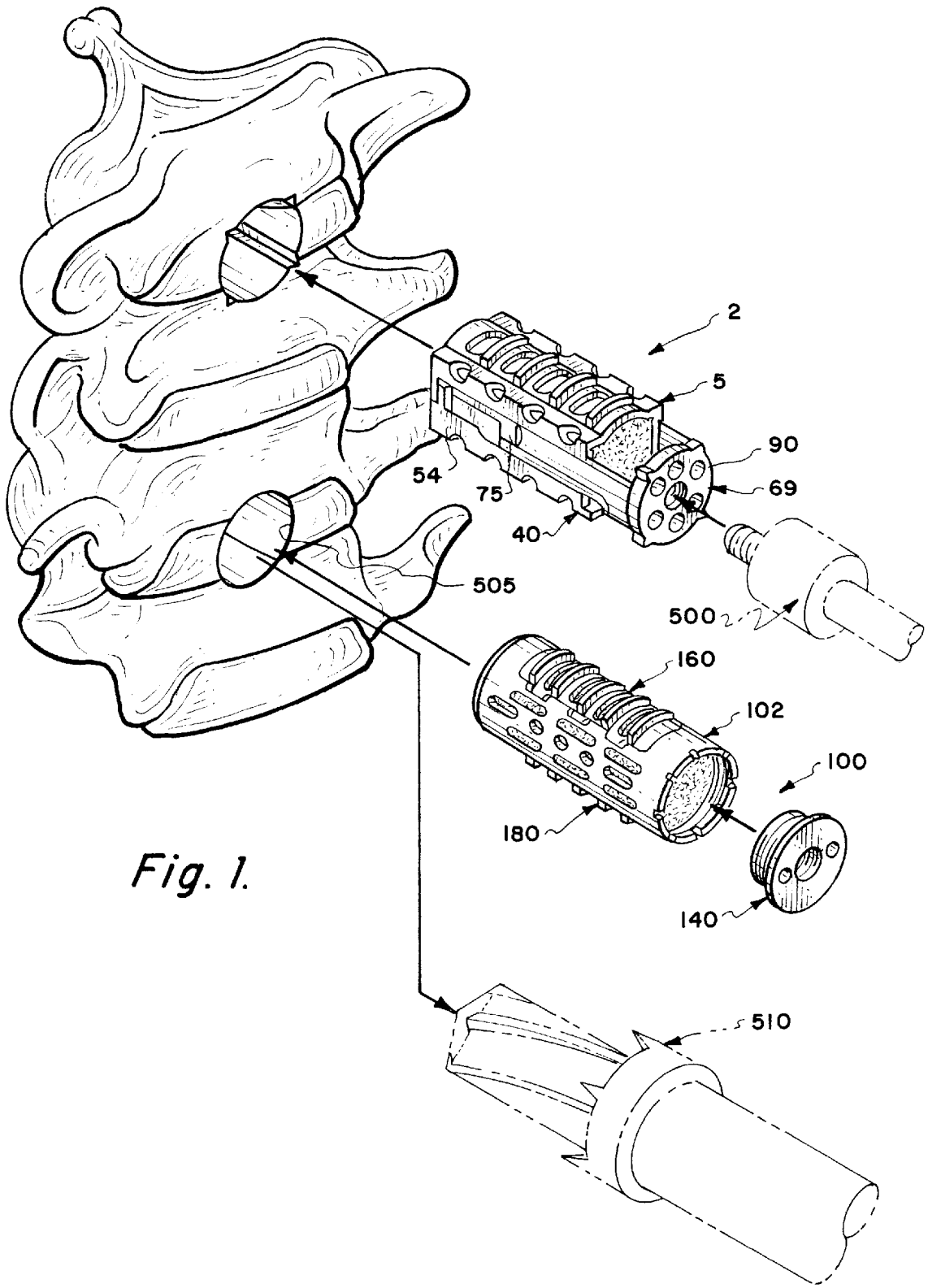
FIG. 1 is a perspective view of the first or box, and second or cylinder, embodiments of the present expandable spinal implant invention indicating where each implant could be implanted in the cervical vertebrae of a patient, and with both embodiments in the open position.

The present invention will now be discussed in greater detail. FIGS. 1 and 2 illustrate the first embodiment in relation to the patient's spine. FIGS. 1–5 illustrate the first embodiment of the present spinal implant invention. The first embodiment which is labelled number 2 in the drawings is an expandable spinal implant as are the other three implants comprising the present invention and described herein. The first embodiment 2 is referred to as the box implant and includes three interlocking parts, which are clearly illustrated in the perspective exploded view in FIG. 5. The three interlocking parts are the superior section 5, the inferior section 40, and the U-shaped expander cap 70. When the three parts interlock, the implant is symmetrical about its vertical medial longitudinal axis. This symmetry also applies to each of the three parts. The superior section 5, the inferior section 40 and the cap 70 are each symmetrical about their respective vertical medial longitudinal axes.

The box implant 2 is a generally box-shaped housing formed by mating together three separate parts. They are the superior section 5, the inferior section 40, and the expander cap 70.

The superior section 5 has a top 7, a pair of mirror image vertical sides 10 and 12 and an upper proximal face portion 15. The vertical side 10 is also referred to as the left vertical side 10, and the other vertical side is also referred to as the right vertical side 12. The proximal face of the box implant is the end directed towards the patient's spine.

The inferior section 40 has a bottom 42, a pair of mirror image vertical sides 51 and 52, and a lower proximal face portion 50. The pair of mirror image vertical sides 10 and 12 on the superior section 5 and the pair of mirror image vertical sides 51 and 52 on the inferior section 8 overlap each other. The vertical side 51 is also referred to as the left vertical side 51, and the vertical side 52 is also referred to as the right vertical side 52. The outside width between the pair of vertical sides 10 and 12 is less than the inside width between the pair of vertical sides 51 and 52. The vertical sides 10 and 12 on the superior section 5 fit inside the vertical sides 51 and 52 on the inferior section. Each of the vertical sides 51 and 52 on the inferior section 40 has a vertical guideway means 56 and 58 respectively. Each one of the vertical sides 10 and 12 on the superior section has locking means 11 and 13 to allow the superior section 5 and the inferior section 40 to expand and contract by sliding outwardly and inwardly transversely relative to each other. The locking means 11 and 13 are illustrated as a mirror image pair of lugs which allow the superior section 5 to slide up and down within the pair of guideway means 56 and 58 on the inferior section 40. The guideway means are illustrated as a pair of vertical slots. This capability allows the two sections 5 and 40 to expand and contract relative to each other. The maximum contraction is limited by the bottoms 57 and 59 of the slots 56 and 58 where the lugs 11 and 13 rest at the maximum contraction. The lugs and slots prevent the two sections 5 and 40 from moving lengthwise relative to each other. The two sections can expand and contract relative to each other, but cannot slide back and forth relative to each other.

Figure 5:
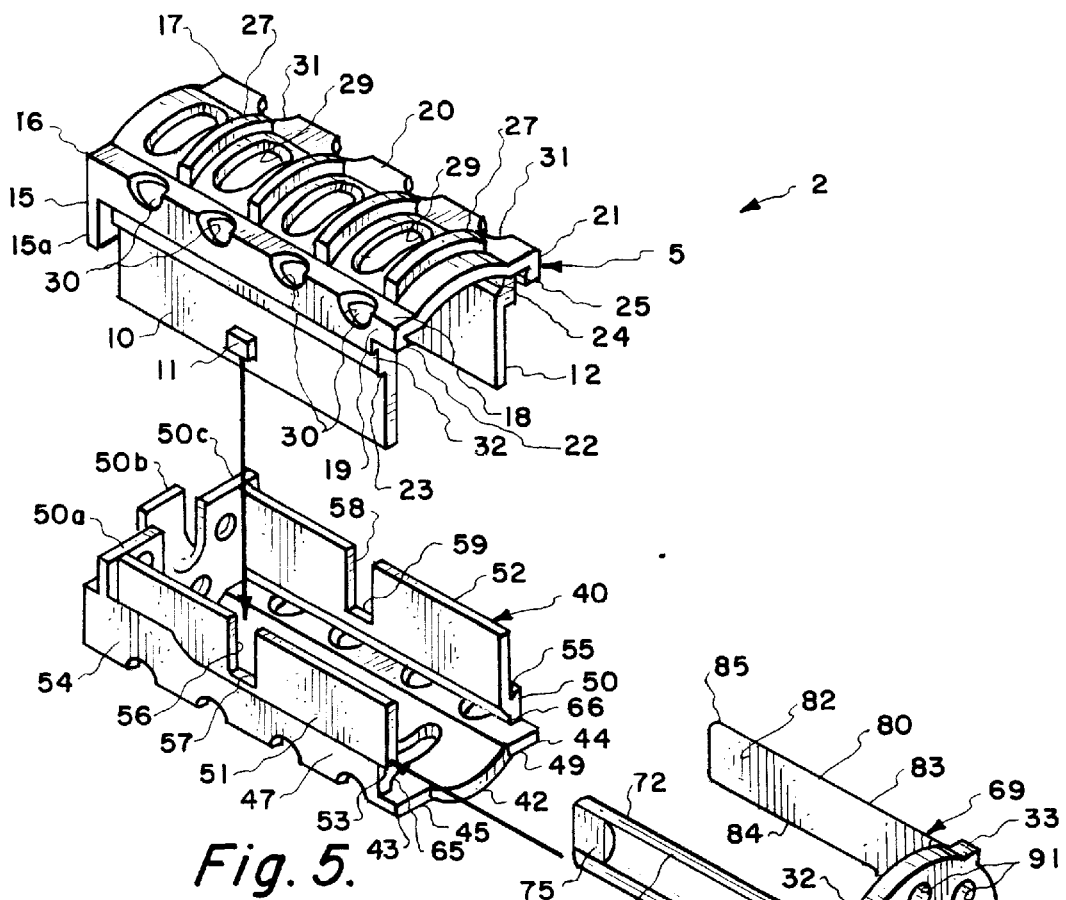
FIG. 5 is a an exploded perspective view of the first or box embodiment of the present spinal implant invention as shown in the closed position in FIG. 3.
Figure 6:
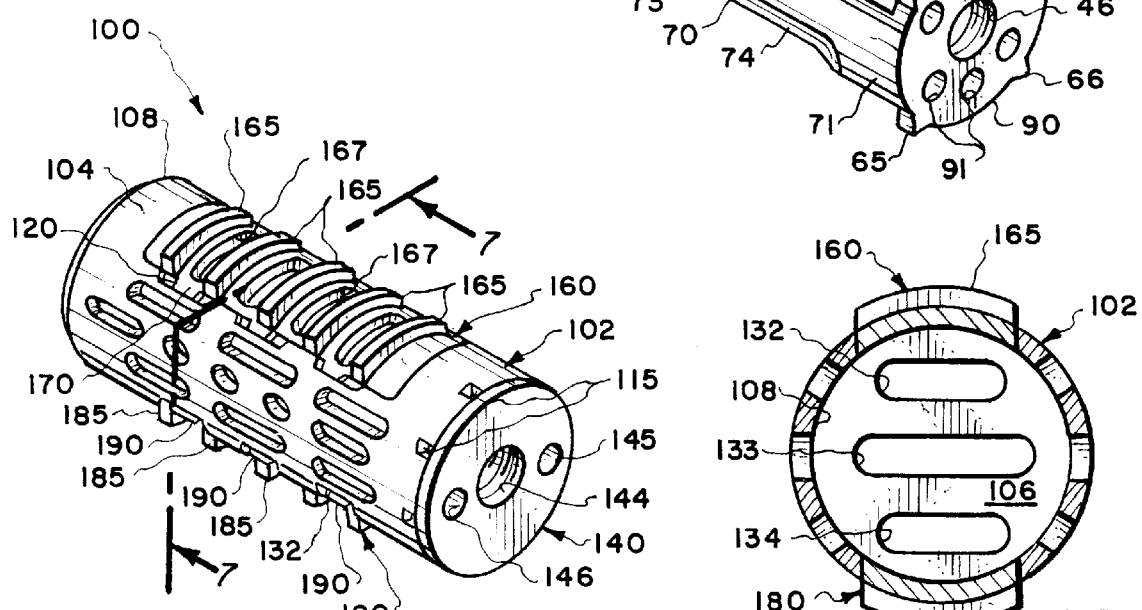
FIG. 6 is a perspective view of the second embodiment of the present spinal implant invention as shown in FIG. 1 with the implant in the closed position.
Figure 7:
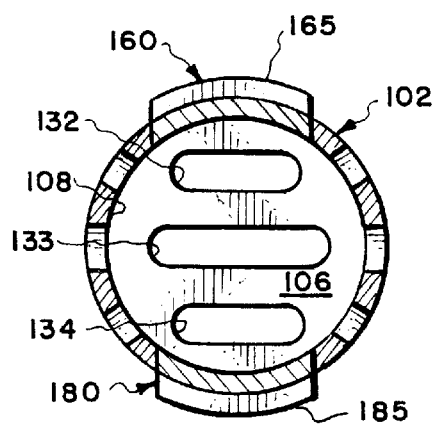
FIG. 7 is a transverse sectional view taken along line 7—7 of FIG. 6.

The top 7 of the superior section 5 is curve-shaped in cross section, and the top has a pair of longitudinal L-shaped edges where the horizontal portion of the top and the vertical portion of the left side 10 and right side 12 meet. The left edge is labelled 16 and the right edge is labelled 17. The left edge 16 includes a flat horizontal portion 18 and a flat vertical portion 19. The right edge 17 includes a flat horizontal portion 20 and a flat vertical portion 21. The vertical portion of each edge 16 and 17 overhangs each vertical sidewall 10 and 12. The pair of sidewalls 10 and 12 are stepped back inwardly from the vertical edges 16 and 17. Running along the bottom of the left flat vertical portion 19 is a check-shaped groove 22 cut upwardly and longitudinally. Below the check-shaped groove 22 is a left-side longitudinal inverted ledge 23. Running along the bottom of the right flat vertical portion 21 is a check-shaped groove 25 cut upwardly and longitudinally. Below the check-shaped groove 25 is a right-side longitudinal inverted ledge 24. FIGS. 4 and 5 clearly illustrate the left check-shaped groove 22, the right check-shaped groove 25, the left inverted ledge 23, the right inverted ledge 24, the left vertical sidewall 10, and the right vertical sidewall 12. FIG. 4 is a transverse sectional view cut along the two guideways 52 and 54 in the inferior section 40.

The top 7 of the superior section 5 has four transverse curved ribs. All four ribs are collectively labelled 27 in the drawings. Four oval-shaped slots are cut transversely in the top and between the ribs 27. The four slots are collectively labelled 29 in the drawings.

The left edge 16 on the superior section 5 has four round openings, collectively labelled 30 in the drawings. The right edge also has four round openings, which are collectively labelled 31 in the drawings. The purpose of these slots 29, left round openings 30, and right round openings 31 are discussed in the Summary and Operation of the Invention, infra.

The inside corner of the left edge 16 on the superior section 5 has a left V-shaped longitudinal groove 32 cut into it. The inside corner of the corresponding right edge 17 also has a right V-shaped longitudinal groove 33 cut into it.

The mid portion of the bottom 42 of the inferior section 40 is a convex curve-shape in cross section. The bottom has a pair of spaced apart longitudinal L-shaped corner edges where the horizontal portions of the bottom and the vertical portions of the left vertical side 45 and the right vertical side 45 meet. The left corner edge is labelled 43 and the right corner edge is labelled 44. The left corner edge 43 includes a flat bottom horizontal portion 45 and a flat vertical portion 47. The right corner edge 44 includes a flat bottom horizontal portion 49 and a flat vertical portion 50, which is illustrated in FIG. 3 The vertical portion of each corner edge 43 and 44 overhangs each lower vertical sides 51 and 52. The pair of lower sides 51 and 52 are stepped back inwardly from the vertical side portions 47 and 50. The upper edge of the left flat vertical portion 47 has a check-shaped groove 53 cut downwardly and running longitudinally along the upper edge. The left vertical portion 47 has a riser 54 towards the proximal end of the lower section 40. The upper edge of the right flat vertical portion 50 has a check-shaped groove 55 cut downwardly and running longitudinally along the upper edge. The right vertical portion 50 also has a riser 60 at the proximal end of the lower section 40. The right riser 60 can be seen in FIG. 18. FIGS. 4 and 5 clearly illustrate the lower left check-shaped groove 53, the lower right check-shaped groove 55, the vertical left side 51, and the vertical lower right side 52. FIG. 4 is a transverse sectional view cut along the two guideways 56 and 58 in the inferior section 40.

Figure 20:
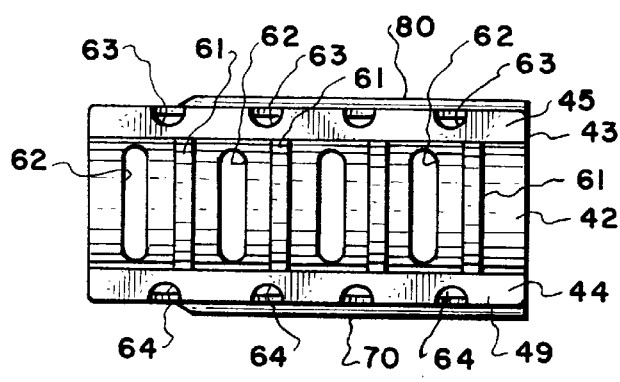
FIG. 20 is a bottom plan view of the box implant shown in FIG. 17. The top plan view is identical to the bottom plan view as shown.

The bottom of the box implant 2 is illustrated in FIG. 20. The bottom 42 of the inferior section 40 has four transverse curved ribs. All four ribs are collectively labelled 61 in the drawings. Four oval-shaped slots are cut transversely in the bottom and between the ribs 61. The four slots are collectively labelled 62 in the drawings. The lower left edge 43 has four round openings, collectively labelled 63 in the drawings. The lower right edge 44 also has four round openings, which are collectively labelled 64 in the drawings. The purpose of these slots 62, lower left openings 63, and lower right openings 64 are to allow bone growth within the implanted implant and is discussed in the Summary and Operation of the Invention, infra.

The inside corner of the lower left edge 43 has a V-shaped longitudinal groove 65 cut into it. The inside corner of the corresponding lower right edge 44 also has a V-shaped longitudinal groove 66 cut into it. The four V-shaped grooves 32,33,65, and 66 are clearly illustrated in the FIG. 4 cross-sectional view.

Figure 18:
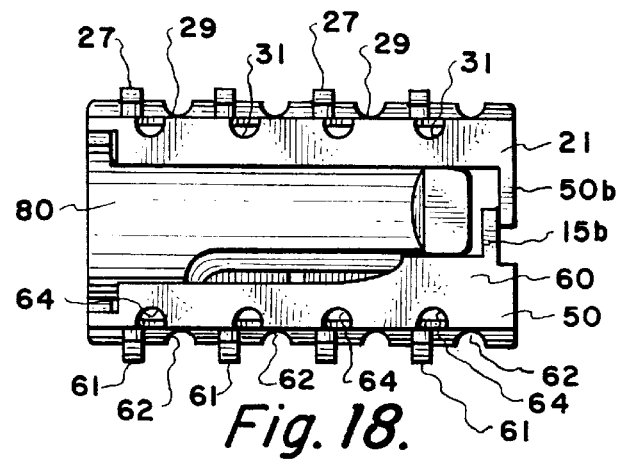
FIG. 18 is a right side elevational view of the box implant shown in FIG. 17. The left side elevational view is identical to the right side view as shown.
Figure 19:
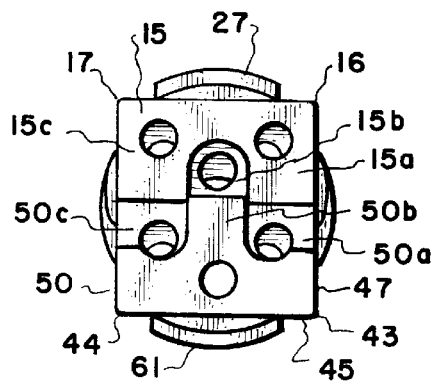
FIG. 19 is a distal or rear elevational view of the box implant shown in FIG. 17.

The proximal vertical face of the box implant 2 has a generally flat vertical face as illustrated in FIGS. 18 and 19 when the superior section 5 and inferior section 40 are joined together. The proximal face 15 of the superior section 5 and the proximal face 50 of the inferior section 40 each have three complementary vertical interlocking tabs. The three vertical tabs on the superior section 5 extend downwardly and collectively form the proximal vertical wall. The three tabs are labelled 15a, 15b, and 15c in the drawings. FIG. 5 shows the left tab 15a. FIG. 18 illustrates all three vertical tabs. The middle tab 15b is stepped distally or inwardly relative to the other two side tabs 15a and 15c. The inferior section 40 has vertical upwardly extending tabs 50a, 50b, and 50c. FIG. 5 clearly illustrates tabs 50a, 50b, and 50c. The middle tab 50b is stepped proximally or outwardly relative to the two side tabs 50a and 50c. The superior and inferior sets of tabs interlock to form a flat vertical proximal wall. The inner face of superior left outer tab 15a lies flush and against the outer face of inferior left outer tab 50a. The outer face of superior middle tab 15b lies flush and against the inner face of inferior middle tab 50b. The inner face of superior right outer tab 15c lies flush and against the outer face of inferior right outer tab 50c.

The box implant 2, which is the first embodiment, also has a mirror image pair of exterior vertical longitudinal channels where the two pair of vertical sides on the superior section and the inferior section overlap. The left channel is defined by the inferior left check-shaped groove 53, the superior left check-shaped groove 22, and the left vertical exterior side 51. The right channel is defined by the inferior right check-shaped groove 55, the superior right check-shaped groove 25 and the right vertical exterior side 52. As previously stated, both left and right channels are slideably expandable.

The box implant 2 also includes the third interlocking part which is a one piece expander. The expander can be described as a generally U-shaped expander 69 formed by a pair of opposed prongs 70 and 80, and an integral sealing cap 90. The expander 69 is used for coupling with the superior section 5 and inferior section 40 which comprise the other two interlocking parts which form the box implant 2. The pair of opposed prongs 70 and 80 are positionable in the pair of mirror image vertical channels on either side of the sections 5 and 40 to force both sections 5 and 40 to expand slightly apart as the cap 90 abuts against the proximal ends of sections 5 and 40. The cap 90 seals off the open end of the box implant 2. The expander 69 is symmetrical about its medial longitudinal vertical plane. The prongs 70 and 80 are mirror images of each other. Each prong has a vertical flat inner face and a convex outer face. Both faces merge to form upper and lower edges. The upper and lower edges of each prong cooperate with the four check-shaped grooves 22, 25, 53 and 55 formed in the box implant 2. The left prong 70 has a curved outer face 71, a flat inner face 72, an upper edge 73, a lower edge 74, and a flat proximal tip 75. The right prong 80 has a curved outer face 81, a flat inner face 82, and upper edge 83, a lower edge 84, and a flat proximal tip 85. The riser portion 54 on the lower section cooperates with the flat tip 75 on the left prong. The length of the left prong from the tip 75 to the face 90 is the same as the length of the lower portion from the open end edge to the stop 50A. Likewise, the length of the right prong from the tip 85 to the face 90 is the same as the length of the lower portion from the open end edge to the stop 5OB.

After the surgeon has made the intervertebral hole in the patient's spine as illustrated in FIG. 1, the implant 2 is packed full with bone chips and perhaps other organic matter. The expander 69 is partially slipped on to the two sections again as illustrated in FIG. 1. The two sections are at their resting minimum height. The implant 2 is inserted fully into the hole until the proximal end is below the surface of the adjacent vertebrae. Then the expander is pushed and locked into place on the implant until the cap forms a flush front surface. As the tips of the expander reaches the risers 54 and 60 but before the stop limits at 50A and 50B on the implant, the two sections expand as shown in FIG. 2 so that the top and bottom transverse ribs penetrate the bottom and top surface of the hole to lock the implant into place. The two sections expand because the heights of both flat tips 75 and 85 are greater the clearance between the two check shaped grooves at this area proximally from the risers. The two tips 75 and 85 wedge themselves between the two grooves to permanently secure the expander with the inferior and superior sections.

FIGS. 1,2, and 6–8 illustrate the second embodiment 100 of the present spinal implant invention. The second embodiment 100 can be described as a cylinder-shaped expandable spinal implant. The second embodiment 100 comprises four components. They are a hollow housing 102, a cap 140, an upper separate removable arcuate section 160, and a lower separate removable arcuate section 180. The cylinder-shaped implant is symmetrical about its axial vertical longitudinal plane, or its axial horizontal longitudinal plane. The hollow housing is labeled 102 in the drawings. The housing is formed by a cylinder-shaped wall 104, a disc-shaped integral sealed proximal end 106, and an opposite distal circular open end 108. The sealed proximal end 106 has three horizontal slots 132, 133 and 134 cut into its face. These slots are illustrated in the cross-sectional view in FIG. 7. The wall has a plurality of small ports and slots. These ports and slots formed in the housing allow for bone growth to occur after implantation of the implant in the patient. The open end 108 of the hollow housing 102 has a means for securing the cap 140. The means for securing the cap is illustrated as an internal threaded surface 110 just inside the open end of the housing and cut into the inner wall of the housing. The removable cap means, illustrated as a circular cap 140, is threadably secured to the open end 108 of the housing 102. The cap has an outer slightly dome-shaped face 141 and a smaller thin concentric cylinder section 142 extending from the underside of the cap 140. The diameter of the cap 140 is the same as the diameter of the outer wall 104 of the cylinder-shaped housing 102. The ring-shaped rim on the underside of the cap 140 has the same dimensions as the face 109 of the housing so that when the cap 140 is screwed onto the end of the housing 102, the rim of the cap 140 lies flush against the face 111 of the housing and forms a sealed end for the housing without any overhang. The face 109 of the housing has eight notches 115 cut therein. The notches will prevent the cap 140 from unscrewing long after the surgery.

The concentric threaded cylinder section 142 on the cap 140 is externally threaded and is complementary with the internal threads 110 in the open end of the housing 102. The diameter of the concentric section 142 is the same as the diameter of the inner wall of the housing.

The cap 140 has a threaded center bore 144. This bore is used to receive the threaded tip of an instrument, which in turn is used to thread the cap 140 into the housing after the housing and arcuate sections 160 and 180 have been positioned into the surgical hole previously drilled in the patient's adjacent vertebrae. The interior of the implant 100 is packed with bone chips just before the cap 140 is screwed onto the end of the implant. The cap compresses the bone chips, which in turn force the arcuate sections 160 and 180 outwardly against the wall of the surgical drill hole to prevent the implant from loosening long after the surgery. The proximal end of an example of a typical instrument is shown in broken lines in FIG. 1 and is labeled 500. The cap also has a pair of small holes 145 and 146. These holes and the center bore 144 allow bone and soft tissue to grow into the implant 100 after the operation. The end result is the implant and the adjacent vertebrae fuse together. The surgical drill hole 505 for receiving the implant 100 and the tip of the instrument used for placing the implant in the hole are illustrated in FIG. 1.

Figure 8:
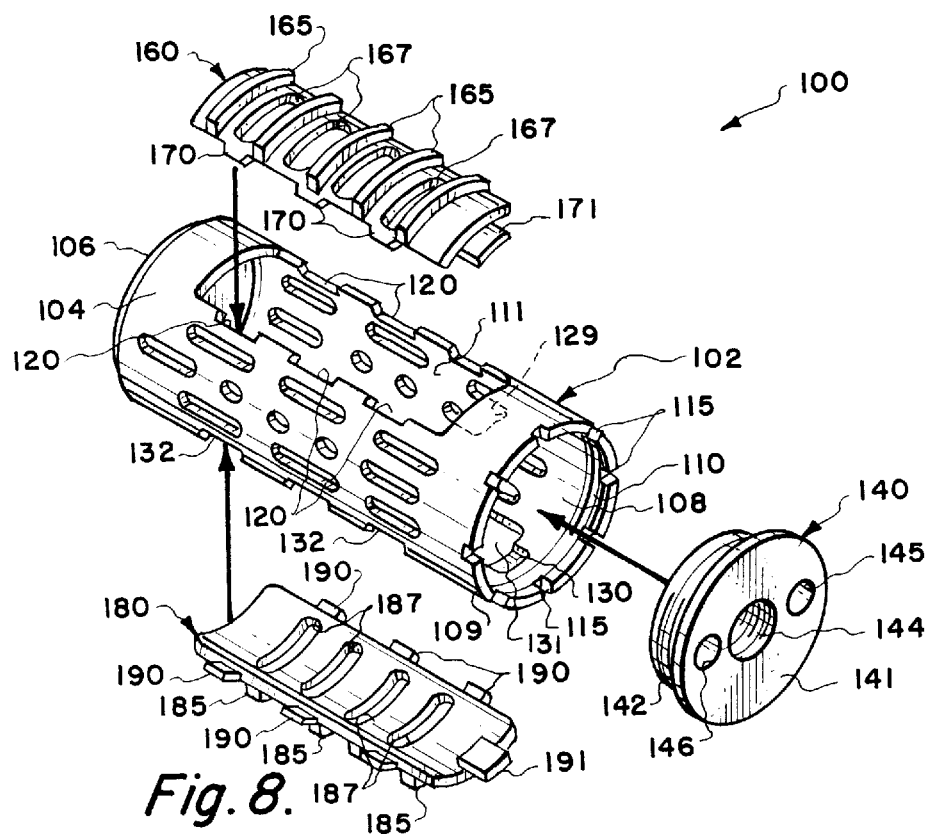
FIG. 8 is an exploded perspective view of the second embodiment of the present spinal implant invention as is also shown in FIGS. 1, 6 & 7.

The housing 104 has a large upper generally rectangular opening 111 located longitudinally in the wall 104 of the housing 102 for receiving the upper arcuate section 160. The arcuate section is positioned in the rectangular opening 111 in the wall 104 of the housing 102. The upper arcuate section 160 and the housing area around the rectangular opening together have locking means for locking the arcuate section 160 in the large rectangular opening 111 in the wall and sealing the opening. The upper arcuate section 160 has an outer surface and an inner surface. The outer surface has a plurality of transverse arcuate ribs. FIG. 8 illustrates five equally spaced apart ribs collectively labeled 165 in the drawings. FIG. 8 also illustrates one slotted opening between adjacent ribs 165. Four transverse slotted openings are disclosed and are collectively labeled 167 in the drawings. The slots 167 allow for bone and tissue penetration, bone and tissue growth and fusion after the cylinder implant is surgically implanted in a patient, as shown in FIGS. 1–2. Both longitudinal edges of the rectangular opening 111 in the housing 102 includes 6 spaced apart notches cut into the edges, three on either side. The notches are collectively labeled 120 and are illustrated in FIG. 8. Both longitudinal edges appear from the side as crenelations. The upper arcuate section 160 has six tabs that are complementary with the notches 120. The tabs are collectively labeled 170 and are illustrated in FIG. 8. The tabs allow the upper arcuate section 160 to seat itself in the rectangular opening 111 in the cylinder housing to cover the opening and remain in place without falling into the housing. Each tab 170 sits in its respective notch 120. The distal end of the arcuate section further has a locking lug 171 which rests in an indentation 129 in the inner wall at the distal transverse edge of the opening 111. The indentation 129 can be seen in cross section in FIG. 1. The locking lug 171 and indentation 129 help to prevent the arcuate section 160 from separating from the housing.

The housing 104 also has a lower large generally rectangular opening 131 located longitudinally in the wall 104 of the housing 102 for receiving the lower arcuate section 180. The lower rectangular opening 131 is a mirror image of the upper rectangular opening 111. The arcuate section is positioned in the rectangular opening 131 in the wall 104 of the housing 102. The distal tip of opening 131 is visible in FIG. 8. The lower arcuate section 180 and the housing area around the rectangular opening together have locking means for locking the arcuate section 180 in the large rectangular opening 131 in the wall and sealing the opening.

The lower arcuate section 180 has an outer surface and an inner surface. The outer surface has a plurality of transverse arcuate ribs. FIG. 8 illustrates the ends of five equally spaced apart ribs collectively labeled 185 in the drawings. FIG. 8 also illustrates one slotted opening between adjacent ribs 185. The four transverse slotted openings are disclosed and are collectively labeled 187 in the drawings. The slots 187 allow for bone and tissue penetration, bone and tissue growth and fusion after the cylinder implant 100 is surgically implanted in a patient, as shown in FIGS. 1–2.

Both longitudinal edges of the rectangular opening 131 in the housing 102 includes 6 spaced apart notches cut into the edges, three on either side. The lower notches are collectively labeled 132. The lower left notches are illustrated in FIG. 8. Both longitudinal edges appear from the side as crenelations. The lower arcuate section 180 has six tabs that are complementary with the notches 132. The tabs are collectively labeled 190 and are illustrated in FIG. 8. The tabs allow the lower arcuate section 180 to seat itself in the rectangular opening 131 in the cylinder housing to cover the opening and remain in place without falling into the housing. Each tab 190 sits in its respective notch 132. The distal end of the arcuate section further has a locking lug 191 which rests in an indentation 130 in the inner wall at the distal transverse edge of the opening 111. The indentation 130 can be seen in FIG. 8. The locking lug 191 and indentation 130 help to prevent the lower arcuate section 180 from separating from the housing 102.

The upper and lower arcuate sections 160 and 180 can expand slightly away from the housing 102 as shown in FIG. 2. The proximal ends will tilt slightly relative to the housing 102. Prior to placing the implant 100 in the surgical drill hole, the housing is packed full of bone chips as is graphically illustrated in FIG. 1. As the cap 140 is screwed into the housing 102, it compresses the bone chips forcing the two arcuate sections 160 and 180 outwardly at the proximal end of the implant 100. The top surfaces and edges of the transverse ribs 167 on the upper arcuate section 160 and the transverse ribs 197 on the lower arcuate section 180 frictionally engage the walls of the drill hole to prevent the implant from loosening and unscrewing months and years after the surgery has been performed.

Figures 9, 10:
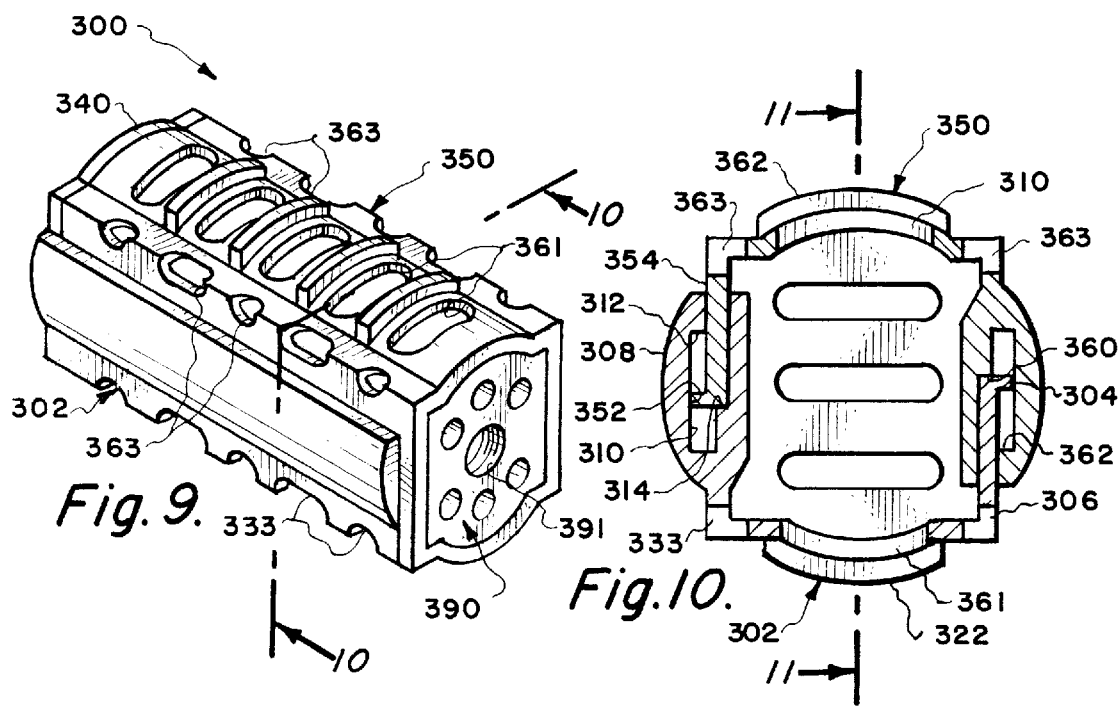
FIG. 9 is a perspective view of the third or shell embodiment of the present invention.
FIG. 10 is a transverse sectional view taken along the line 10—10 of FIG. 9.
Figure 14:
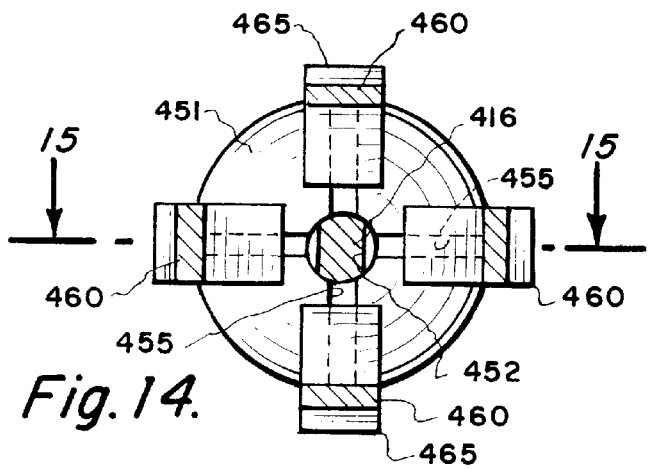
FIG. 14 is a transverse sectional view taken along line 14—14 of FIG. 13.
Figure 15:
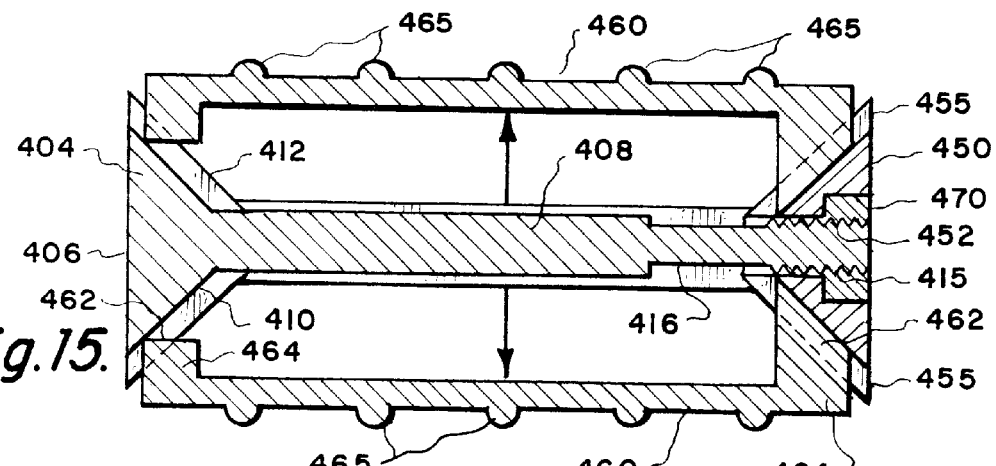
FIG. 15 is a longitudinal sectional view taken along line 15—15 of FIG. 14.
Figure 16:
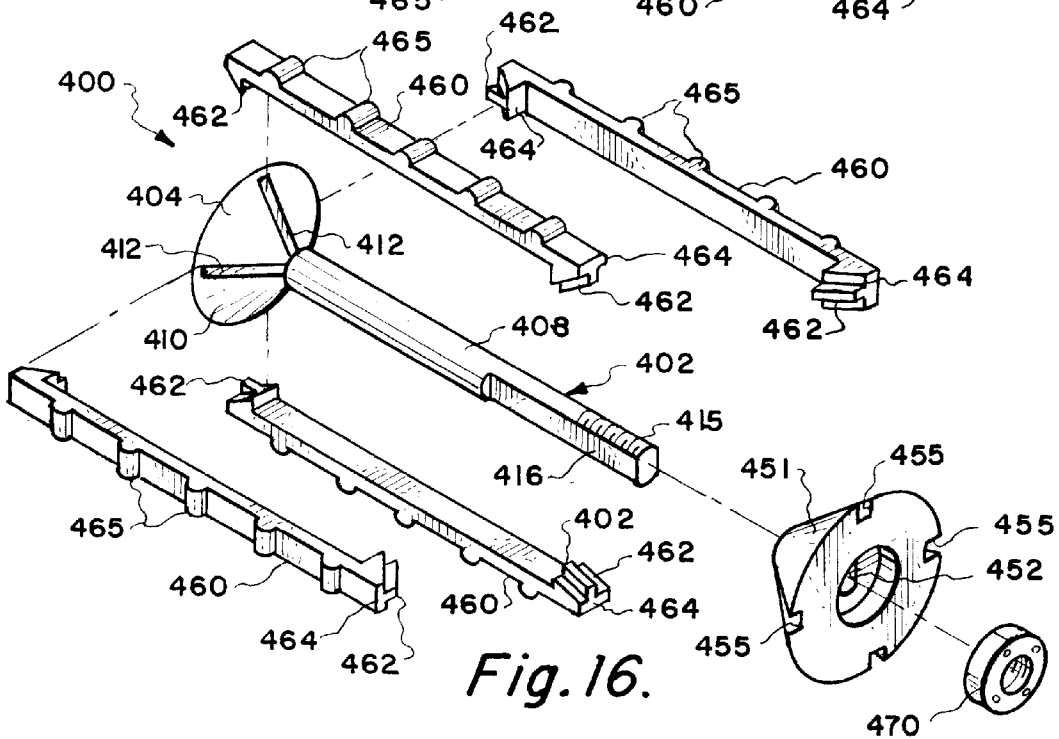
FIG. 16 is an exploded sectional view of the fourth embodiment of the present invention.
Figure 17:
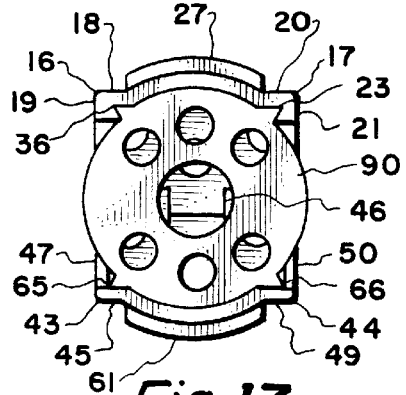
FIG. 17 is a proximal or front elevational view of the box implant shown in the perspective view in FIG. 3.

FIGS. 9, 10, 11 & 12 illustrate the third embodiment 300 of the present spinal implant invention. FIG. 9 is a perspective view of the third or shell embodiment of the present invention. FIG. 10 is a transverse sectional view taken along the line 10—10 of FIG. 9. FIG. 11 is a longitudinal sectional view taken along the line 11—11 of FIG. 10. FIG. 12 is an exploded sectional view of the third embodiment of the present invention. The third embodiment can be described as a two-piece shell expandable spinal implant. The third embodiment shell implant has three separate components. They are the lower shell 302, the upper shell 350, and the locking distal plate 390. All three components are clearly illustrated in the exploded perspective view in FIG. 12. The distal end of the lower shell 302 has a vertical plate 340 secured to it. The upper and lower shells are fastened together by means of two expansion joints, one on each side of the implant. The expansion joints allow for a limited range of transverse contraction and expansion and also longitudinal movement relative to each other. The expansion joints are clearly shown in the cross-sectional view of FIG. 10. The expansion joints are nearly mirror images of each other. If the implant as shown in FIG. 10 were rotated about its longitudinal axis 180 degrees, one would see the same view as presently shown in FIG. 10. The lower shell 302 has a horizontal rail 304 running along the upper edge of the right sidewall 306. The left sidewall 308 has a upwardly open horizontal slot 310 or guideway for receiving the rail 352 on the left sidewall 354 of the upper shell 302. Inside the guideway 310 is shown a lower horizontal step 314 upon which the rail 352 rests when the pair of shells are at their minimum contraction. A horizontal ledge 312 positioned above the step 314 in the guideway 310 acts to limit the maximum expansion of the pair of shells. The ledge 312 will stop the rail 352 from moving past it to prevent transverse separation of the pair of shells.

The upper shell has a similar structure. The upper shell 350 has horizontal rail 352 running along the lower edge of the left sidewall 354. The right sidewall 356 has a downwardly open horizontal slot 358 or guideway for receiving the rail 304 on the right sidewall 306 of the lower shell 302. Inside the guideway 358 is shown an upper horizontal ledge 360 upon which the upper shell rests on the rail 304 when the pair of shells are at their minimum contraction. A horizontal step 362 positioned below the ledge 360 in the guideway 358 acts to limit the maximum expansion to the pair of shells. The step 362 will stop the rail 304 from moving past it to prevent transverse separation of the pair of shells. FIGS. 9 and 10 illustrate the pair of shells at their minimum. They cannot contract more than that shown in the two figures. The proximal plate 340 is configured for that contraction so that the perimeter of the plate is flush with the perimeter of the pair of shells. The locking plate 390 would also be configured to seal the distal opening for this minimum contraction. It is to be understood that the plates 340 and 390 could be configured to accommodate and seal the ends of the pair of shells at their maximum expansion. Maximum expansion would occur when the rail 352 abuts against the ledge 312 in the left sidewall, and the rail 304 abuts against the step 362 in the right sidewall. It is also to be understood that the distances between the ledge 312 and the step 314, and the ledge 360 and the step 362 could be less than that shown and described. This would result in only slight expansion capability. The cross-sectional view of FIG. 10 shows the capability of much expansion between the pair of shells.

The top outer surface of the upper shell 350 has four transverse curved ribs collectively labelled 362 in the drawings. Five oval-shaped slots are cut transversely in the top between the ribs. The five slots are collectively labelled 361 in the drawings. The upper left and right edges of the upper shell each have five round openings and are collectively labelled 363 in the drawings. The top surface of the upper shell 350 is similar or nearly identical to the top surface of the superior section of the box implant 2 previously discussed.

The bottom outer surface of the lower shell 302 has four transverse curved ribs collectively labelled 322 in the drawings. Five oval-shaped slots are cut transversely in the bottom between the ribs. The five slots are collectively labelled 321 in the drawings. The bottom left and right edges of the lower shell each have five round openings and are collectively labelled 333 in the drawings. The bottom outer surface of the lower shell 302 is similar or nearly identical to the bottom surface of the inferior section of the box implant 2 previously discussed. The purpose of these slots 361 and 321, and the holes 333 and 363 are to allow bone growth within the implant and is discussed in the Summary and Operation of the Invention, infra.

The plate 390 has a center threaded hole 391 for attaching to the tip of the surgical instrument 500 to assist the surgeon in implanting the implant. The holes or fenestrations in the plates 340 and 390 also allow for bone growth within the implant.

The curved ribs 322 and 362 serve the same function as the curved ribs in the box implant. They dig into the upper and lower surfaces of the surgical hole to seat the implant and to prevent it from loosening long after the operation. The surgeon packs the implant full of bone chips and then inserts the implant. The surgeon then packs more bone chips into the interior space of the implant, then forces the plate to snap into place in the distal end of the implant. The compaction of the bone chips forces the pair of shells to expand in the surgical hole. The plate 390 and the distal end of the pair of shells have means for locking the plate in the open end to seal it. The means could be slots and tabs, or a compression fit for example.

FIGS. 13–16 illustrate the fourth embodiment 400 of the present spinal implant invention. The proximal end is the end towards the patient's spine and the distal end is the end toward the surgeon. The fourth embodiment 400 can be described as a reel-shaped expandable spinal implant. The implant 400 has six separate components. They are: a bolt; a nut; and four support braces. The framework for the implant includes a bolt 402 having a flat cone-shaped head 404. The flat outer surface of the bolt 404 forms the circular proximal end of the implant 400. The axial shank of the bolt 402 forms the central rod 408 of the implant 400. The cone-shaped head of the bolt has a round flat top 406, and an opposite cone-shaped surface 410 having an apex where the proximal end of the central rod 408 is secured. The cone 410 surface has at least two and preferably four equally spaced radial axial grooves 412 cut into the cone surface of the cone-shaped bolt head 404.

The central rod 408 has a threaded end 415 and opposed secant flat sections 416 removed from the surface of the central rod 408 towards the distal end of the rod. A cone-shaped cap 450 has a slotted bore 452 for slideably engaging the central rod 408 of the implant along the length where the secant flat sections 416 are located. The secant flats 416 and the slotted bore 452 prevent the cap 450 from rotating about the axis of the central rod 408. At least two and preferably four equally spaced radial axial grooves 455 are cut into the cone surface of the coneshaped cap 450. The cap 450 and the cone-shaped bolt head 410 are nearly mirror images of each other. They are axially aligned and in an opposed relationship with each other. The apexes of both cones face each other.

The four axial radial slots 412 in the cone-shaped surface of the bolt head 404 and the four axial radial slots 455 in the cone-shaped surface 451 of the cap 450 are in the same circumferential radial alignment relative to the axis of the central rod 408. The net result is that there are four pair of radial slots facing each other. Each pair is designed to receive the ends of a support brace. Four circumferential support braces 460 are positioned axially for engagement between the bolt head 410 and the cap 450. The four braces are identical and are collectively labeled 460 in the drawings. Each support brace 460 is slightly less than the combined length of the bolt head 404 and the central rod 408. Each end of each support brace has a beveled tip 462 and a small key 464 for slidably engaging with the radial slots 412 and 455 on both the cap 450 and the bolt head 404. The angle of the beveled tips 462 is the same as the angle of the sloping cone surfaces 410 and 451 on both the cap 450 and the bolt head 404. Five transverse ribs 465 are positioned on the outer surface of each support brace 460. Each support brace 460 is symmetrical about its vertical and transverse cross section. This symmetry allows the support brace 460 to be positioned interchangeably with any pair of the radial slots 412 and 455.

A threaded nut 470 can engage the threaded end of the central rod 408. By tightening the nut, the cap 450 is caused to slide towards the bolt head 404. The keys 464 on the ends of the braces 460 slide outwardly and radially to expand the four braces 460 until the implant is securely locked into position in the surgical hole in the vertebrae previously drilled and prepared by the surgeon for receiving the implant 400. Prior to tightening the nut 470, the open space between the central rod 408 and the four braces 460 is packed with bone chips so that the implant will fuse with the adjacent vertebrae after implantation. Obviously, many modifications and variants of the present invention are possible in light of the above teachings. It is therefore to be understood that the full scope of the invention is not limited to the details disclosed herein, but may be practiced otherwise than as specifically described.

What is claimed is:

1. A Box-shaped expandable spinal implant comprising:
   a generally box-shaped housing formed by mating a superior section and an inferior section;
   a superior section comprising a top, a pair of mirror image vertical sides, and an upper proximal face;
   an inferior section comprising a bottom, a pair of mirror image vertical sides, and a lower proximal face;
   said pair of mirror image vertical sides on said superior section and said pair of mirror image vertical sides on said inferior section overlap each other and have guide way means and locking means to allow said upper section and said lower section to slideably expand transversely relative to each other;
   said superior and inferior sections forming a closed end and an open end;
   a pair of exterior longitudinal channels formed where said pair of vertical sides overlap;
   a generally U-shaped expander formed by a pair of opposed prongs and a sealing cap for coupling with said superior and inferior sections;
   said pair of opposed prongs on said expander positionable in said pair of expandable channels on the sides of said superior and inferior sections to force said sections slightly apart as said cap abuts said open end of said sections and said U-shaped expander locks said sections together while said cap on said expander seals off said open end of said implant.

2. The implant as recited in claim 1 further comprising:
   a plurality of transverse ridges on the top and bottom of said implant; and
   a plurality of slots formed between said ridges.

3. The implant as recited in claim 2 further comprising:
   a plurality of holes on the four longitudinal edges of said implant;
   a plurality of holes o n said sealing cap; and
   a plurality of holes on said proximal end of said implant.

* * * * *